US010251876B2

(12) United States Patent
Wang et al.

(10) Patent No.: US 10,251,876 B2
(45) Date of Patent: Apr. 9, 2019

(54) METHOD FOR TREATING TUMOUR, PHARMACEUTICAL COMPOSITION AND MEDICINAL KIT

(71) Applicants: CHIA TAI TIANQING PHARMACEUTICAL GROUP CO., LTD., Jiangsu (CN); ADVENCHEN LABORATORIES NANJING LTD, Jiangsu (CN)

(72) Inventors: Shanchun Wang, Jiangsu (CN); Xunqiang Wang, Jiangsu (CN); Hongmei Gu, Jiangsu (CN); Ping Dong, Jiangsu (CN); Hongjiang Xu, Jiangsu (CN)

( * ) Notice: Subject to any disclaimer, the term of this patent is extended or adjusted under 35 U.S.C. 154(b) by 0 days.

(21) Appl. No.: 15/315,655

(22) PCT Filed: Jun. 5, 2015

(86) PCT No.: PCT/CN2015/080863
§ 371 (c)(1),
(2) Date: Dec. 1, 2016

(87) PCT Pub. No.: WO2015/185012
PCT Pub. Date: Dec. 10, 2015

(65) Prior Publication Data
US 2017/0182027 A1    Jun. 29, 2017

(30) Foreign Application Priority Data

Jun. 6, 2014 (CN) .......................... 2014 1 0250113

(51) Int. Cl.
*A61K 31/4709*  (2006.01)
*A61K 9/20*  (2006.01)
*A61K 9/48*  (2006.01)

(52) U.S. Cl.
CPC ............ *A61K 31/4709* (2013.01); *A61K 9/20* (2013.01); *A61K 9/48* (2013.01)

(58) Field of Classification Search
CPC ..... A61K 31/4709; A61K 9/48; C07D 239/74
(Continued)

(56) References Cited

U.S. PATENT DOCUMENTS 7,667,039 B2    2/2010  Garcia-Echeverria et al.
8,148,532 B2    4/2012  Chen
(Continued)

FOREIGN PATENT DOCUMENTS

CN    101809012    8/2010
CN    102344438    2/2012
(Continued)

OTHER PUBLICATIONS

Traina et al, Optimizing Chemotherapy Dose and Schedule by Norton-Simon Mathematical Modeling, Breast Dis (2010), vol. 31(1), pp. 1-21.*

(Continued)

*Primary Examiner* — Craig D Ricci
*Assistant Examiner* — Janet L. Coppins
(74) *Attorney, Agent, or Firm* — Knobbe, Martens, Olson & Bear, LLP

(57) ABSTRACT

The present invention provides 1-[[[4-(4-fluoro-2-methyl-1H-indol-5-yl)oxy-6-methoxyquinolin-7-yl]oxy]methyl]cyclopro-pylamine used for combating a tumor. Specially, the present invention refers to method for treating tumor, pharmaceutical composition and medicinal kit related to the described compound. Administrating the compound with a suitable dosage regimen can not only make the patient's plasma concentration maintain the level of 100 ng/ml or lower, but also achieve effects of treatments and obtain benefits for various tumours.

15 Claims, 1 Drawing Sheet

(58) Field of Classification Search
USPC .......................................................... 514/312
See application file for complete search history.

(56) References Cited

U.S. PATENT DOCUMENTS

| | | |
|---|---|---|
| 9,550,781 B2 | 1/2017 | Xiao |
| 9,725,439 B2 | 8/2017 | Xiao et al. |
| 9,751,859 B2 | 9/2017 | Chen |
| 9,968,597 B2 | 5/2018 | Zhang et al. |
| 2010/0105696 A1 | 4/2010 | Garcia-Echevrria et al. |
| 2016/0326138 A1 | 11/2016 | Chen et al. |
| 2017/0174687 A1 | 6/2017 | Chen et al. |
| 2017/0182027 A1 | 6/2017 | Wang |
| 2017/0202828 A1 | 7/2017 | Zhang et al. |
| 2017/0304290 A1 | 10/2017 | Wang et al. |
| 2018/0002311 A1 | 1/2018 | Chen et al. |

FOREIGN PATENT DOCUMENTS

| | | | |
|---|---|---|---|
| WO | WO 2006/122806 | 11/2006 | |
| WO | WO 2008/112407 A1 | 9/2008 | |
| WO | WO 2008/112408 | 9/2008 | |
| WO | WO 2008112407 A1 * | 9/2008 | ........... C07D 239/74 |
| WO | WO2008112407 A1 * | 9/2008 | ........... C07D 239/74 |
| WO | WO 2009/155527 | 12/2009 | |
| WO | WO 2010/105761 | 9/2010 | |
| WO | WO 2014/113616 | 7/2014 | |

OTHER PUBLICATIONS

Traina et al, British J. of Cancer (2004), vol. 90, pp. 2250-2255.*
Eskens et al, J Clin Oncology (2009), vol. 27(25), pp. 4169-4176.*
Bello, E. et al., E-3810 Is a Potent Dual Inhibitor of VEGFR and FGFR that Exerts Antitumor Activity in Multiple Preclinical Models, Cancer Research; 71(4), Feb. 15, 2011.
International Preliminary Report on Patentability and Written Opinion received in International patent application No. PCT/US2014/011948, dated Jul. 21, 2015.
Moreno et al., Clin Transl Oncol (2010) 12:468-472.
Sala, F. et al., Development and validation of a high-performance liquid chromatography—tandem mass spectrometry method for the determination of the novel inhibitor of angiogenesis E-3810 in human plasma and its application in a clinical pharmacokinetic study, Journal of Mass Spectrometry, 2011, 46, pp. 1039-1045.
Traina et al.—Optimizing Chemotherapy Dose and Schedule by Norton-Simon Mathematical Modeling (cited in OA), Breast Dis. (2010) , vol. 31 (1) , pp. 7-18.
Zhou, Y. et al., AL3810, a multi-tyrosine kinase inhibitor, exhibits potent anti-angiogenic and ant-tumor activity via targeting VEGFR, FGFR, and PDGFR, Journal of Cellular and Molecular Medicine, vol. 16, No. 10, 2012 pp. 2321-2330.
XELODA® Prescribing Information; Genentech USA, Inc.,—Xeloda, Mar. 2015.
Han et al., "Anlotinib as a third-line therapy in patients with refractory advanced non-small-cell lung cancer: a multicentre, randomised phase 11 trial (AL TER0302)", 2018, British Journal of Cancer, 118(5), pp. 654-661. (Year: 2018).
National Center for Biotechnology Information. PubChem Compound Database; CI D=25017 411, https://pubchem.ncbi.nlm.nih.gov/compound/25017 411 (accessed Apr. 4, 2018). (Year: 2018).
Sun et al., "Safety, pharmacokinetics, and antitumor properties of anlotinib, an oral multi-target tyrosine kinase inhibitor, in patients with advanced refractory solid tumors", 2016, Journal of Hematology & Oncology, 9: 105; DOI 10.1186/s 13045-016-0332-8. (Year: 2016).

* cited by examiner

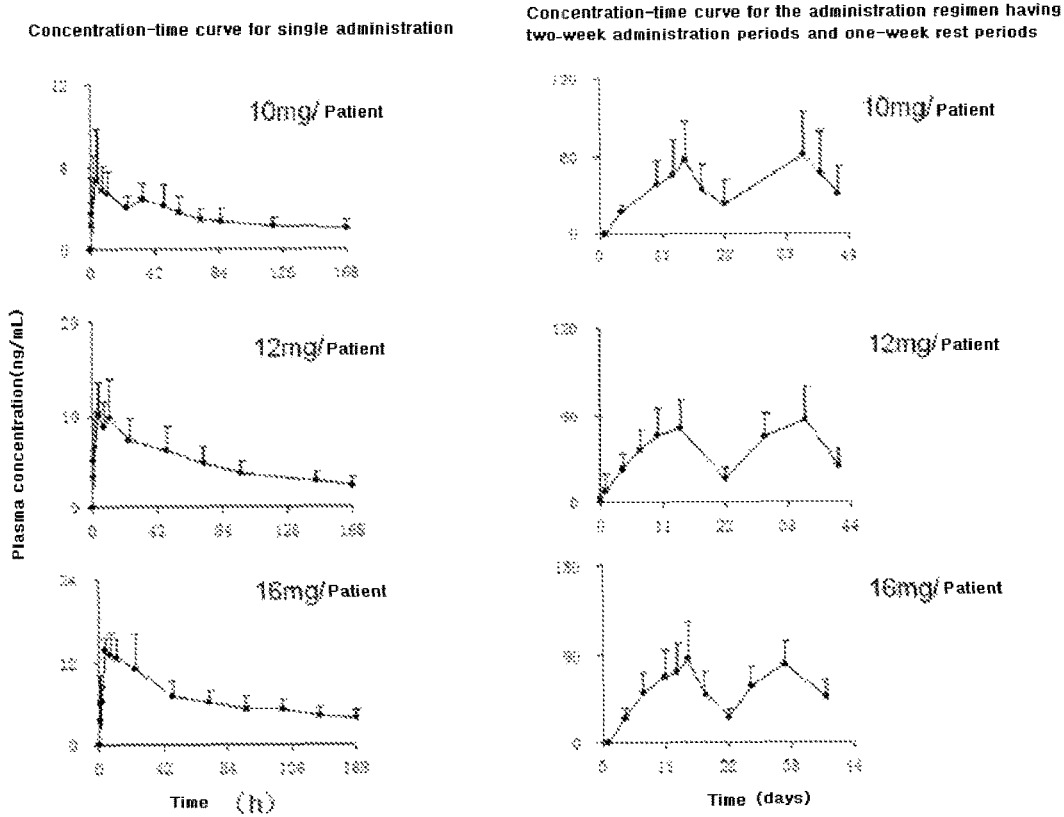

METHOD FOR TREATING TUMOUR, PHARMACEUTICAL COMPOSITION AND MEDICINAL KIT

INCORPORATION BY REFERENCE TO ANY PRIORITY APPLICATIONS

This application is the U.S. National Phase of International Application PCT/CN2015/080863, filed Jun. 5, 2015, which claims the benefit of priority to Chinese Application No. 201410250113.7, filed on Jun. 6, 2014, the disclosures of each of which are hereby incorporated by reference in their entireties.

FIELD OF THE INVENTION

The present invention relates to a method for treating tumour, a pharmaceutical composition and a medicinal kit, and specifically relates to 1-[[[4-(4-fluoro-2-methyl-1H-indol-5-yl)oxy-6-methoxyquinolin-7-yl]oxy]methyl]cyclopropylamine which can be used as an angiogenesis inhibitor.

BACKGROUND OF THE INVENTION

WO2008112407 discloses anti-tumour compounds, and also discloses processes for their preparation, pharmaceutical compositions containing them as active ingredients, methods for treating the disease states associated with angiogenesis, such as tumours associated with protein tyrosine kinases. The above-mentioned compounds can inhibit the activities of tyrosine kinases such as VEGFr, EGFr and PDGF, and they may also be irreversible inhibitors of tyrosine kinases. Its Description also discloses treatment regimens for said spiro substituted compounds and the daily oral administration dosage is preferably 0.01-200 mg/Kg. The daily dosage for administration by injection including intravenous, intramuscular, subcutaneous and parenteral injections and use of infusion technique is preferably 0.01-200 mg/Kg. The daily rectal administration dosage is preferably 0.01-200 mg/Kg. The daily vaginal administration dosage is preferably 0.01-200 mg/Kg. The daily topical administration dosage is preferably 0.01-200 mg, administered 1-4 times daily. The preferred transdermal concentration is that required to maintain a daily dose of 0.01-200 mg/Kg. The daily inhalation dosage is preferably 0.01-200 mg/Kg. The Examples therein discloses formulations of a part of the spiro substituted compounds, including capsules and liquid formulations. The amount of the active ingredients in the capsules is 100 mg.

Chinese patent application CN102344438A discloses Forms A, B and C crystal of the compound of 1-[[[4-(4-fluoro-2-methyl-1H-indol-5-yl)oxy-6-methoxyquinolin-7-yl]oxy]methyl]cyclopropylamine dihydrochloride, and the preparation method, and also discloses a pharmaceutical composition comprising the crystal forms. And it points out that the pharmaceutical compositions suitable for oral administration includes tablets, capsules, dusts, granulates, drip pills, pastes, powders, tinctures and the like, and tablets and capsules are preferred. Among them, the tablets can be common tablets, dispersible tablets, effervescent tablets, sustained release tablets, controlled release tablets or enteric coated tablets, and the capsules can be common capsules, sustained release capsules, controlled release capsules or enteric coated capsules. They can be prepared with well-known routine pharmaceutical excipients in the art by conventional methods. The amount of active substances in one unit formulation of oral tablets and capsules should vary depend on treatment conditions of patients and specific administration route. For example, the unit formulation for oral administration can conveniently contain 1 mg-100 mg of active substances, preferably 3 mg-30 mg of active substances.

Tyrosine kinases are a group of enzymes that catalyze phosphorylation of tyrosine residues in proteins, and they play an important role in the cellular signal transduction. Meanwhile, they involve in regulation, signal transmission and development of normal cells, and they are also closely related to proliferation, differentiation, migration and apoptosis of tumour cells. Many receptor tyrosine kinases are correlated with the formation of tumours, and according to the different structures of the extracellular domain, they can be classified as epidermal growth factor receptor, platelet-derived growth factor receptor, vascular endothelial growth factor receptor, fibroblast growth factor receptor and so on. Currently, tyrosine kinase inhibitors marketed in China are imatinib mesylate, sunitinib malate, erlotinib hydrochloride, dasatinib, lapatinib mesylate, nilotinib, gefitinib and icotinib hydrochloride.

SUMMARY OF THE INVENTION

In the first aspect, the present invention provides a method for treating cancer, which comprises administrating a daily dosage of 5 mg-20 mg of Compound I or pharmaceutically acceptable salts thereof to patients, preferably 8 mg-20 mg of Compound I or pharmaceutically acceptable salts thereof, more preferably 8 mg-16 mg of Compound I or pharmaceutically acceptable salts thereof, further preferably 10 mg-16 mg of Compound I or pharmaceutically acceptable salts thereof, further preferably 10 mg-14 mg of Compound I or pharmaceutically acceptable salts thereof. In one embodiment, administrating a daily dosage of 10 mg of Compound I or pharmaceutically acceptable salts thereof. In one embodiment, administrating a daily dosage of 12 mg of Compound I or pharmaceutically acceptable salts thereof. In one embodiment, administrating a daily dosage of 14 mg of Compound I or pharmaceutically acceptable salts thereof. In one embodiment, administrating a daily dosage of 16 mg of Compound I or pharmaceutically acceptable salts thereof. The chemical name of Compound I is 1-[[[4-(4-fluoro-2-methyl-1H-indol-5-yl)oxy-6-methoxyouinolin-7-yl]oxy]methyl]cyclopropylamine, which has the following structural formula:

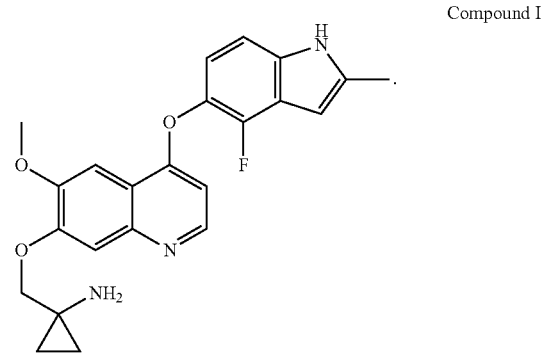 [SMILES: COc1cc2c(Oc3ccc4[nH]c(C)cc4c3F)ccnc2cc1OCC1(N)CC1]

Compound I

Compound I can be administrated in the free base form thereof, and also can be administrated in the form of salts, hydrates and prodrugs thereof (the prodrugs will be converted into the free base form of Compound I in vivo). For example, Compound I is administrated in the form of pharmaceutically acceptable salts. Within the scope of the present invention, the salts can be produced from different organic acids and inorganic acids according to well-known processes in the art.

In some embodiments, Compound I is administrated in the form of hydrochloride thereof. In some embodiments, Compound I is administrated in the form of monohydrochloride thereof. In some embodiments, Compound I is administrated in the form of dihydrochloride thereof. In some embodiments, Compound I is administrated in the crystal form of hydrochloride thereof. In a certain embodiment, Compound I is administrated in the crystal form of dihydrochloride thereof.

Compound I or pharmaceutically acceptable salts thereof can be administrated via various administration routes, and the routes include, but not limited to, the one selected from the following routes: orally, parenterally, intraperitoneally, intravenously, intraarterially, transdermally, sublingually, intramuscularly, rectally, transbuccally, intranasally, via inhalation, vaginally, intraoccularly, via local administration, subcutaneously, intraadiposally, intraarticularly, intraperitoneally or intrathecally. In a certain embodiment, the administration is performed orally.

Compound I or pharmaceutically acceptable salts thereof can be administrated one or more times daily. Preferably, a therapeutically effective amount of Compound I or pharmaceutically acceptable salts thereof is administrated once per day. Administration can be performed in the form of single dosage or multiple dosages, and the administration can preferably be performed in the form of single dosage once per day. The above-mentioned dosage level of Compound I or pharmaceutically acceptable salts thereof is administrated once per day, and such an administration regimen improves patient's compliance. In one embodiment, the administration is performed once per day, and optionally the administration is performed once per day in the form of single dosage. In one embodiment, the administration is performed once per day in the form of single dosage of oral capsule.

Surprisingly, the inventors found that, during administration, therapeutic effects of Compound I or pharmaceutically acceptable salts thereof can be maintained without daily administration, namely, the interval administration of Compound I or pharmaceutically acceptable salts thereof would provide the therapeutically effective amount of Compound I in plasma.

The interval administration includes administration periods and rest periods, and during the administration periods, Compound I or pharmaceutically acceptable salts thereof can be administrated one or more times daily. For example, Compound I or pharmaceutically acceptable salts thereof is administrated daily in an administration period, and then the administration is stopped for a period of time in a rest period, followed by an administration period and then a rest period, such an administration regimen can be repeated. Among them, the ratio of the administration periods to the rest periods in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

In some embodiments, the interval administration of Compound I or pharmaceutically acceptable salts thereof can not only make the patient's plasma concentration maintain the level of 100 ng/ml or lower so as to get drug accumulation degree controlled, but also achieve effects of treatments and obtain benefits for various tumours.

In some embodiments, the tumours include, but not limited to, liver cancer, breast cancer, kidney cancer, colorectal cancer, non-small cell lung cancer, gastrointestinal stromal tumour, medullary thyroid carcinoma and soft tissue sarcoma.

In the second aspect, the present invention provides a method for treating tumours, comprising an interval administration of Compound I or pharmaceutically acceptable salts thereof to patients.

The interval administration can provide a therapeutically effective amount of Compound I in plasma. The interval administration includes administration periods and rest periods, and during the administration periods, Compound I or pharmaceutically acceptable salts thereof is administrated one or more times daily. For example, Compound I or pharmaceutically acceptable salts thereof is administrated daily in an administration period, and then the administration is stopped for a period of time in a rest period, followed by an administration period and then a rest period, and so forth.

Wherein, the ratio of the administration periods to the rest periods in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

In some embodiments, a daily dosage of 5 mg-20 mg of Compound I or pharmaceutically acceptable salts thereof was administered to patients, preferably 8 mg-20 mg of Compound I or pharmaceutically acceptable salts thereof, more preferably 8 mg-16 mg of Compound I or pharmaceutically acceptable salts thereof, further preferably 10 mg-16 mg of Compound I or pharmaceutically acceptable salts thereof, further preferably 10 mg-14 mg of Compound I or pharmaceutically acceptable salts thereof. In one embodiment, administrating a daily dosage of 10 mg of Compound I or pharmaceutically acceptable salts thereof. In one embodiment, administrating a daily dosage of 12 mg of Compound I or pharmaceutically acceptable salts thereof. In one embodiment, administrating a daily dosage of 14 mg of Compound I or pharmaceutically acceptable salts thereof. In one embodiment, administrating a daily dosage of 16 mg of Compound I or pharmaceutically acceptable salts thereof.

In some embodiments, Compound I is administered in the form of hydrochloride thereof. In some embodiments, Compound I is administered in the form of monohydrochloride thereof. In some embodiments, Compound I is administered in the form of dihydrochloride thereof. In some embodiments, Compound I is administered in the crystal form of hydrochloride thereof. In a certain embodiment, Compound I is administered in the crystal form of dihydrochloride thereof.

Compound I or pharmaceutically acceptable salts thereof can be administered via various administration routes, and the routes include, but not limited to, the one selected from the following routes: orally, parenterally, intraperitoneally, intravenously, intraarterially, transdermally, sublingually, intramuscularly, rectally, transbuccally, intranasally, via inhalation, vaginally, intraoccularly, via local administration, subcutaneously, intraadiposally, intraarticularly, intraperitoneally or intrathecally. In a certain embodiment, the administration is performed orally.

The administration can be performed in the form of single dosage or multiple dosages, and the administration can preferably be performed in the form of single dosage once per day. Compound I or pharmaceutically acceptable salts thereof is administered once per day, such an administration regimen improves patient's compliance. In one embodiment, the administration is performed once per day, and optionally the administration is performed once per day in the form of single dosage. In one embodiment, the administration is performed once per day in the form of single dosage of oral capsule.

In some embodiments, the interval administration of Compound I or pharmaceutically acceptable salts thereof can not only make the patient's plasma concentration maintain the level of 100 ng/ml or lower so as to get drug accumulation degree controlled, but also achieve effects of treatments and obtain benefits for various tumours.

In some embodiments, the tumours include, but not limited to, liver cancer, breast cancer, kidney cancer, colorectal cancer, non-small cell lung cancer, gastrointestinal stromal tumour, medullary thyroid carcinoma and soft tissue sarcoma.

In the third aspect, the present invention provides a method for treating tumours, comprising interval administration of Compound I or pharmaceutically acceptable salts thereof to patients, wherein the plasma concentration of Compound I is 100 ng/ml or lower.

The treatment method can provide the therapeutically effective amount of Compound I in plasma. The interval administration includes administration periods and rest periods, and during the administration periods, Compound I or pharmaceutically acceptable salts thereof can be administered one or more times daily. For example, Compound I or pharmaceutically acceptable salts thereof is administered daily in an administration period, and then the administration is stopped for a period of time in a rest period, followed by an administration period and then a rest period, and so forth.

Among them, the ratio of the administration periods to the rest periods in days is 2:0.5-5, preferably 2:0.5-3, more preferably 2:0.5-2, and most preferably 2:0.5-1. In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

In some embodiments, a daily dosage of 5 mg-20 mg of Compound I or pharmaceutically acceptable salts thereof was administered to patients, preferably 8 mg-20 mg of Compound I or pharmaceutically acceptable salts thereof, more preferably 8 mg-16 mg of Compound I or pharmaceutically acceptable salts thereof, further preferably 10 mg-16 mg of Compound I or pharmaceutically acceptable salts thereof, further preferably 10 mg-14 mg of Compound I or pharmaceutically acceptable salts thereof. In one embodiment, administrating a daily dosage of 10 mg of Compound I or pharmaceutically acceptable salts thereof. In one embodiment, administrating a daily dosage of 12 mg of Compound I or pharmaceutically acceptable salts thereof. In one embodiment, administrating a daily dosage of 14 mg of Compound I or pharmaceutically acceptable salts thereof. In one embodiment, administrating a daily dosage of 16 mg of Compound I or pharmaceutically acceptable salts thereof.

In some embodiments, Compound I is administered in the form of hydrochloride thereof. In some embodiments, Compound I is administered in the form of monohydrochloride thereof. In some embodiments, Compound I is administered in the form of dihydrochloride thereof. In some embodiments, Compound I is administered in the crystal form of hydrochloride thereof. In a certain embodiment, Compound I is administered in the crystal form of dihydrochloride thereof.

Compound I or pharmaceutically acceptable salts thereof can be administered via various administration routes, and the routes include, but not limited to, the one selected from the following routes: orally, parenterally, intraperitoneally, intravenously, intraarterially, transdermally, sublingually, intramuscularly, rectally, transbuccally, intranasally, via inhalation, vaginally, intraoccularly, via local administration, subcutaneously, intraadiposally, intraarticularly, intraperitoneally or intrathecally. In a certain embodiment, the administration is performed orally.

The administration can be performed in the form of single dosage or multiple dosages, and the administration can preferably be performed in the form of single dosage once per day. Compound I or pharmaceutically acceptable salts thereof is administrated once per day, such an administration regimen improves patient's compliance. In one embodiment, the administration is performed once per day, and optionally the administration is performed once per day in the form of single dosage. In one embodiment, the administration is performed once per day in the form of single dosage of oral capsule.

In some embodiments, the tumours include, but not limited to, liver cancer, breast cancer, kidney cancer, colorectal cancer, non-small cell lung cancer, gastrointestinal stromal tumour, medullary thyroid carcinoma and soft tissue sarcoma.

In the forth aspect, the present invention provides a pharmaceutical composition, which contains 5 mg-20 mg of Compound I or pharmaceutically acceptable salts thereof. Preferably containing 8 mg-20 mg of Compound I or pharmaceutically acceptable salts thereof. More preferably containing 8 mg-16 mg of Compound I or pharmaceutically acceptable salts thereof. further preferably containing 10 mg-16 mg of Compound I or pharmaceutically acceptable salts thereof. Most preferably containing 10 mg-14 mg of Compound I or pharmaceutically acceptable salts thereof. In one embodiment, the pharmaceutical composition contains 10 mg of Compound I or pharmaceutically acceptable salts thereof. In one embodiment, the pharmaceutical composition contains 12 mg of Compound I or pharmaceutically acceptable salts thereof. In one embodiment, the pharmaceutical composition contains 14 mg of Compound I or pharmaceutically acceptable salts thereof. In one embodiment, the pharmaceutical composition contains 16 mg of Compound I or pharmaceutically acceptable salts thereof.

Compound I or pharmaceutically acceptable salts thereof can be contained in pharmaceutical compositions suitable for various administration routes. For example, Compound I or pharmaceutically acceptable salts thereof can be contained in the pharmaceutical compositions suitable for the following administration routes: orally, parenterally, intraperitoneally, intravenously, intraarterially, transdermally, sublingually, intramuscularly, rectally, transbuccally, intranasally, via inhalation, vaginally, intraoccularly, via local administration (for example by a catheter or stent), subcutaneously, intraadiposally, intraarticularly, intraperitoneally or intrathecally. Compound I or pharmaceutically acceptable salts thereof can be formulated in various pharmaceutically acceptable pharmaceutical composition, including oral form (e.g., tablets, capsules, dusts, granules, drip pills, pastes and powders), injectable form (e.g., subcutaneous, intravenous, intramuscular and intraperitoneal injections), drip infusion, external application form (e.g., nasal spray formulations, transdermal formulations, ointments and so on) and suppositories (e.g., rectal suppositories and vaginal suppositories). These different pharmaceutically acceptable pharmaceutical compositions can be prepared with pharmaceutically acceptable carriers routinely used in pharmaceutical industry by the known technology routinely used in pharmaceutical industry.

In some embodiments, the pharmaceutical composition is solid formulation suitable for orally administration. For example, the composition may be in the form of tablet or capsule. In some special embodiments, the composition is in the form of capsule.

The pharmaceutical composition can be administrated in the form of single dosage or multiple dosages. In one embodiment, the pharmaceutical composition can be administrated in the form of single dosage or multiple dosages once per day.

Further, the present invention provides a pharmaceutical composition formulated in the form of single dosage, wherein the form of single dosage contains 5 mg to 20 mg of Compound I or pharmaceutically acceptable salts thereof. Preferably, the form of single dosage contains 8 mg-20 mg of Compound I or pharmaceutically acceptable salts. Preferably, the form of single dosage contains 8 mg-16 mg of Compound I or pharmaceutically acceptable salts. Preferably, the form of single dosage contains 10 mg-16 mg of Compound I or pharmaceutically acceptable salts. More preferably, the form of single dosage contains 10 mg-14 mg of Compound I or pharmaceutically acceptable salts. In some embodiments, the form of single dosage contains 10 mg of Compound I or pharmaceutically acceptable salts thereof. In some embodiments, the form of single dosage contains 12 mg of Compound I or pharmaceutically acceptable salts thereof. In some embodiments, the form of single dosage contains 14 mg of Compound I or pharmaceutically acceptable salts thereof. In some embodiments, the form of single dosage contains 16 mg of Compound I or pharmaceutically acceptable salts thereof.

Unless indicated otherwise, Compound I or pharmaceutically acceptable salts thereof described herein includes the form of free base of Compound I, the form of salts of Compound I, the form of hydrate of Compound I and the form of hydrate of the salts thereof. The special form of salts used may includes, but not limited to salts formed from benzoic acid, toluenesulfonic acid, hydrochloric acid.

In some embodiments, Compound I or pharmaceutically acceptable salts thereof is the form of hydrochloride of Compound I. In some embodiments, Compound I or pharmaceutically acceptable salts thereof is the form of monohydrochloride of Compound I. In some embodiments, Compound I or pharmaceutically acceptable salts thereof is the form of dihydrochloride of Compound I. In some embodiments, Compound I or pharmaceutically acceptable salts thereof is the crystal form of hydrochloride of Compound I. In a certain embodiment, Compound I or pharmaceutically acceptable salts thereof is the crystal form of dihydrochloride of Compound I.

The pharmaceutical composition can be optionally used for treating the diseases which are regulated by tyrosine kinases and the diseases which are related to abnormal activity transduction pathways of tyrosine kinases. In some embodiments, the pharmaceutical composition can be used for treating the diseases mediated by VEGFR-1 (Flt-1), VEGFR-2(KDR), VEGFR3 (Flt-4), c-kit, PDGFR or FGFR1. In some embodiments, the pharmaceutical composition can be used for treating tumours including but not limited to liver cancer, breast cancer, kidney cancer, colorectal cancer, non-small cell lung cancer, gastrointestinal stromal tumour, medullary thyroid carcinoma and soft tissue sarcoma.

WO2008112407 discloses the daily oral administration dosage, but when long term and uninterrupted administration was performed, the incidence of adverse reactions (especially severe adverse reactions) of the drug is increased, which results in deterioration and out of control of the conditions, so that the administration has to be stopped. When administrating the dosage of the pharmaceutical composition described therein, the invention surprisingly found that, under the condition that the therapeutic effects are maintained and the diseases are effectively treated, an interval administration can be performed, which provides a convalescence to patients, so as to greatly reduce the incidence of adverse reactions (especially severe adverse reactions) of the drug, dramatically increase safety of the drug, and improve patient's compliance.

When administration is performed, the above dosage level of the pharmaceutical composition can maintain the therapeutic effects without daily administration, which is unexpected. That is to say, the interval administration of the pharmaceutical composition to patients can provide the therapeutically effective amount of Compound I in plasma.

The interval administration includes administration periods and rest periods, and during the administration periods, Compound I or pharmaceutically acceptable salts thereof can be administrated one or more times daily. For example, Compound I or pharmaceutically acceptable salts thereof is administrated daily in an administration period, and then the administration is stopped for a period of time in a rest period, followed by an administration period and then a rest period, such an administration regimen can be repeated. Among them, the ratio of the administration periods to the rest periods in days is 2:0.5-5, preferably 2:0.5-3, more preferably 2:0.5-2, and most preferably 2:0.5-1.

In some embodiments, the administration is continuously performed for 2 weeks and rest for 2 weeks. In some embodiments, the administration is continuously performed once daily for 14 days and rest for 14 days, followed by continuous administrating once daily for 14 days and resting for 14 days, such an administration regimen with two-week continuous administration periods and two-week rest periods can be repeated many times.

In some embodiments, the administration is continuously performed for 2 weeks and rest for 1 week. In some embodiments, the administration is continuously performed once daily for 14 days and rest for 7 days, followed by continuous administrating once daily for 14 days and resting for 7 days, such an administration regimen with two-week continuous administration periods and one-week rest periods can be repeated many times.

In some embodiments, the administration is continuously performed for 5 days and rest for 2 days. In some embodiments, the administration is continuously performed once daily for 5 days and rest for 2 days, followed by continuous administrating once daily for 5 days and resting for 2 days, such an administration regimen with five-day continuous administration periods and two-day rest periods can be repeated many times.

In some embodiments, the administration of pharmaceutical composition according to the above method can not only make the patient's plasma concentration maintain the level of 100 ng/ml or lower so as to get drug accumulation degree controlled and reduce toxicity, but also achieve effects of treatments and obtain benefits for various tumours.

In the fifth aspect, the present invention also provides a medicinal kit, which comprises the pharmaceutical composition of the present invention comprising Compound I or pharmaceutically acceptable salts thereof, wherein the medicinal kit further comprises instructions, and the instructions includes one or more forms of the following information: displaying disease states at which the administration of the pharmaceutical composition is aimed, storage information of the pharmaceutical composition, administration information and usage information on how to administrate the pharmaceutical composition.

In some embodiments, a medicinal kit is provided, which comprises the pharmaceutical composition of the present invention, and the instructions for interval administration of the pharmaceutical composition to patients. The interval administration includes administration periods and rest periods, and during the administration periods, the pharmaceutical composition can be administrated one or more times per day. For example, the pharmaceutical composition is administrated daily in an administration period, and then the administration is stopped for a period of time in a rest period, followed by an administration period and then a rest period, and so forth. Among them, the ratio of the administration periods to the rest periods in days is 2:0.5-5, preferably 2:0.5-3, more preferably 2:0.5-2, and most preferably 2:0.5-1.

In the sixth aspect, the present invention also provides a medicinal kit, which comprises instructions for usage of the interval administration of Compound I or pharmaceutically acceptable salts thereof when treating tumours. The usage of the interval administration can provide the therapeutically effective amount of Compound I in plasma, and the plasma concentration of Compound I is 100 ng/ml or lower.

The interval administration includes administration periods and rest periods, and during the administration periods, Compound I or pharmaceutically acceptable salts thereof can be administrated one or more times daily. For example, Compound I or pharmaceutically acceptable salts thereof is administrated daily in an administration period, and then the administration is stopped for a period of time in a rest period, followed by an administration period and then a rest period, such an administration regimen can be repeated. Among them, the ratio of the administration periods to the rest periods in days is 2:0.5-5, preferably 2:0.5-3, more preferably 2:0.5-2, and most preferably 2:0.5-1.

The tumours include, but not limited to, liver cancer, breast cancer, kidney cancer, colorectal cancer, non-small cell lung cancer, gastrointestinal stromal tumour, medullary thyroid carcinoma and soft tissue sarcoma.

For all of the above-mentioned embodiments, it should be noted that, these embodiments should be understood as an open mode, which means the methods can includes further actions in addition to those specified, comprising administrating other active pharmaceutical substances to the patients. Similarly, unless indicated otherwise, the pharmaceutical composition and the medicinal kit thereof can further contain other materials, including other active pharmaceutical substances.

Herein, unless indicated otherwise, the dosages and ranges provided therein are based on the molecular weight of the free base form of Compound I.

Herein, the crystal form of the hydrochloride of Compound I includes, but not limited to, Forms A, B and C crystal disclosed in the Chinese patent application CN102344438A, wherein Forms A and B crystal are those which do not contain crystal water and other solvents basically, and Form C crystal is the one containing two molecules of crystal water. In some embodiments, the crystal form of the hydrochloride of Compound I is Form A crystal.

Unless indicated otherwise, for the purpose of the present application, the following terms are intended to have the meanings denoted below as used in the Description and Claims.

"Pharmaceutically acceptable" means that which is useful in preparing a pharmaceutical composition that is generally safe, non-toxic and neither biologically nor otherwise undesirable, and includes that which is acceptable for human pharmaceutical use.

"Pharmaceutically acceptable salts" include, but not limited to acid addition salts formed from inorganic acids such as hydrochloric acid, hydrobromic acid, sulfuric acid, nitric acid, phosphoric acid or the like; or acid addition salts formed from organic acids such as acetic acid, trifluoroacetic acid, propionic acid, caproic acid, heptanoic acid, cyclopentane propionic acid, glycolic acid, pyruvic acid, lactic acid, malonic acid, succinic acid, malic acid, maleic acid, fumaric acid, tartaric acid, citric acid, benzoic acid, cinnamic acid, mandelic acid, methyl sulfonic acid, ethyl sulfonic acid, 1,2-ethanedisulfonic acid, 2-hydroxyethanesulphonic acid, benzenesulfonic acid, p-chlorobenzenesulfonic acid, p-toluenesulfonic acid, 3-phenylpropionic acid, trimethylacetic acid, t-butylacetic acid, dodecyl sulfuric acid, gluconic acid, glutamic acid, hydroxynaphthoic acid, salicylic acid, stearic acid and the like.

"Patients" refer to mammal, preferably human. In some embodiments, the patients are those having failed standard treatment or lacking standard treatment.

"Therapeutically effective amount" means an amount of a compound that, when administered to a subject for treating a disease state, is sufficient to effect such treatment for the disease state.

"Treatment/treating" means any administration of therapeutically effective amount of a compound, and includes:
(1) Inhibiting the disease in humans that is experiencing or displaying the pathology or symptomatology of the disease (i.e., retarding further development of the pathology and/or symptomatology), or
(2) Ameliorating the disease in humans that is experiencing or displaying the pathology or symptomatology of the disease (i.e., reversing the pathology and/or symptomatology).

DESCRIPTION OF DRAWINGS

FIG. 1 shows the concentration-time curve for single administration with two-week administration periods and one-week rest periods regimen.

DETAILED EMBODIMENTS OF THE INVENTION

EXAMPLE 1

1-[[[4-(4-fluoro-2-methyl-1H-indol-5-yl)oxy-6-methoxyquinolin-7-yl]oxy]methyl]cyclopropylamine dihydrochloride

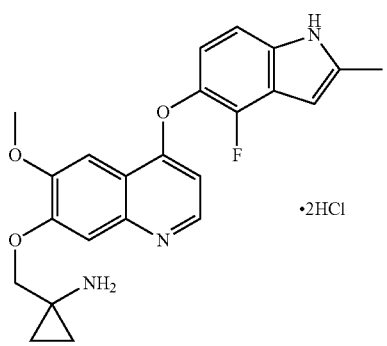 [SMILES: COc1cc2c(Oc3ccc4[nH]c(C)cc4c3F)ccnc2cc1OCC1(N)CC1]

1-[[[4-(4-fluoro-2-methyl-1H-indol-5-yl)oxy-6-methoxyquinolin-7-yl]oxy]methyl]cyclopropylamine was prepared by reference to the method of Example 24 in WO2008112407, and then the title compound was prepared by reference to the preparation method in "Examples of Salt Formation" of the Description of WO2008112407.

EXAMPLE 2

The capsules comprising 1-[[[4-(4-fluoro-2-methyl-1H-indol-5-yl)oxy-6-methoxyquinolin-7-yl]oxy]methyl]cyclopropylamine dihydrochloride (dihydrochloride of Compound I)

| Raw material/excipient names | amount (1000 capsules) |
| --- | --- |
| Dihydrochloride of Compound I | 14.16 g(corresponding to 12 g Compound I) |
| Mannitol | 89 g |
| Microcrystalline cellulose | 138.4 g |
| Hydroxypropyl cellulose | 5.9 g |
| Magnesium stearate | 0.99 g |

Dihydrochloride of Compound I was grinded and sifted with a 80 mesh sieve, and then mixed uniformly with mannitol and hydroxypropyl cellulose; the prescribed amount of microcrystalline cellulose was subsequently added, mixed uniformly and sifted with a 0.8 mm sieve; and finally, the prescribed amount of magnesium stearate was added and mixed uniformly, and the obtained mixture was filled into capsules.

The capsules in which dihydrochloride of Compound I is at different contents can be prepared by reference to the above proportion and formulation.

EXAMPLE 3

Tolerance and Preliminary Therapeutic Effect Study of Administration (1) Tolerance Research The malignant tumor patients those were diagnosed definitely and had failed standard treatment or lacking standard treatment were recruited for phase I study of tolerance and preliminary therapeutic effect. The tolerance was observed when patients were administered 5 mg or 10 mg of the capsules of dihydrochloride of Compound I once daily respectively for at least 2 cycles continuously, wherein each cycle was 28 days. The pharmacokinetic data shows that the drug accumulates obviously in person's plasma after continuously administration of the capsules of dihydrochloride of Compound I.

After the adjustment of the dosage regimen, the malignant tumor patients those were diagnosed definitely and had failed standard treatment or lacking standard treatment were recruited, continuous administrating for 2 weeks and resting for 1 week were applied, i.e., 3 weeks (21 days) was a treatment cycle, and the observation of tolerance was continuously performed and maintained at least 2 cycles (42 days), and the observation of therapeutic effects was performed at the same time.

When the administration was performed at 10 mg once daily, the adverse reactions occurred in 3 patients including grade III or above increased fatty and amylase in 1 case, and grade II asthenia in 1 case, and other grade I adverse reactions including hoarseness in 2 cases, diarrhea and abdominal pain in 1 case, hypertension in 1 case and the like.

Under the condition that the administration was performed at 16 mg once daily, 1 case in 3 patients occurred grade III elevation of blood pressure and asthenia when administrated at the $2^{nd}$ week in the $2^{nd}$ cycle. Other adverse reactions occurred in this research group included grade II hypertension in 1 case, decreased thyroid function in 2 cases, increased ALT in 1 case, grade I increased triglyceride in 2 cases, diarrhea and abdominal pain in 2 cases, hand-foot syndrome in 1 case, hoarseness in 1 case and the like.

When the administration was performed at 12 mg once daily, observe the tolerance and preliminary therapeutic effect study of the capsules of dihydrochloride of Compound I. A total of 18 patients (5 cases of them were out of the group) were observed in this group. The different degrees of adverse reactions occurred during administration. The order of severity was grade I or II, and no grade III or higher adverse reactions occurred. The specific situation included:

Blood fat: increased triglyceride in 8 cases, and increased total cholesterol in 7 cases;

Liver function: increased total bilirubin in 4 cases, increased ALT in 4 cases, increased AST in 5 cases, and increased creatinine in 1 case;

Dermal toxicity: hand-foot skin reaction in 6 cases, and rash in 4 cases;

Endocrine system: hypothyroidism in 7 cases, hyperthyroidism in 2 cases, increased amylase in 3 cases, and increased CK-MB in 2 cases;

Symptoms: asthenia in 6 cases, hoarseness in 4 cases, diarrhea in 6 cases, dizziness and headache in 2 cases, toothache in 3 cases, muscular soreness in 3 cases, nausea and loss of appetite in 3 cases, and tinnitus, fever and insomnia each in 1 case;

Others: hypertension in 5 cases, hematuria in 5 cases, proteinuria in 5 cases, and decreased WBC in 3 cases.

(2) Preliminary Therapeutic Effect

In 12 mg dosage group, 13 cases are being administrated, wherein the longest administration involves 11 cycles, and the shortest administration involves 4 cycles. 3 cases in 5 subjects which stopped administration were evaluated as PD (progression of disease) after 2 cycles and out of the group, 1 case was out of the group after 6 cycles due to PD, and 1 case was evaluated as SD (stable disease) (small) after 4 cycles, and out of the group after 5 cycles due to SAE (serious adverse events).

(3) Overall Therapeutic Effect

Tumor regression was observed in a part of the subjects at 10 mg dose.

18 patients joined in 12 mg group with continuous administration once daily for two weeks and rest for one week, wherein 1 case has not arrived at the time point for evaluating the therapeutic effects, and 1 case among the rest of 17 cases has no target lesion and thus cannot be evaluated. 1 case was PR (partial remission) (9.1%), 11 cases were SD (small) (72.7%), 1 case was SD (large) (9.1%), and 3 cases were PD (9.1%). The disease control rate (DCR) was 76.5%, and PR+SD (small) also achieved 70% or more.

In the group, there are 8 subjects having soft tissue sarcoma, wherein the tumour evaluation of 1 case after 4 cycles was PR, 4 cases were SD, and 3 subjects were PD; there are 6 subjects having medullary thyroid carcinoma, wherein 1 case cannot be evaluated, 4 cases were SD (small), and 1 case was PD; and, the clinical benefit rate of soft tissue sarcoma reached 62%, and the benefit rate of medullary thyroid carcinoma was 80% or more.

The capsules of Compound I dihydrochloride employed the administration regimen with continuous administration for two weeks and rest for one week, the general tolerability was very well, and the adverse reaction was ½ degree; for the therapeutic effects, various tumours can benefit from the treatment of Compound I dihydrochloride.

EXAMPLE 4

Pharmacokinetic Studies

All the solid tumour subjects participating in the tolerance research in Example 3 were performed a monitor of plasma concentration to evaluate pharmacokinetic parameters of the capsule of Compound I dihydrochloride.

(1) Pharmacokinetics of Single Administration

After beginning the tests, the qualified subjects took the capsule of Compound I dihydrochloride once and performed pharmacokinetic studies of single administration. The plasma concentrations of 19 subjects in 3 dose groups (10 mg, 16 mg and 12 mg, respectively) were detected, and FIG. 1 (left) shows the average concentration-time curve of each dose group. Table 1 shows the pharmacokinetic parameters evaluated based on FIG. 1 (left).

TABLE 1

The pharmacokinetic parameters of Compound I

| The pharmacokinetic parameters | Mean (RSD %) | | |
|---|---|---|---|
| | 10 mg/person (n = 4) | 12 mg/person (n = 11) | 16 mg/person (n = 4) |
| $C_{max}$ (ng/ml) | 6.07 (45.2) | 11.3 (32.7) | 16.1 (12.7) |
| $C_{max}$/dosage | 43.4 (45.3) | 64.6 (34.9) | 57.6 (8.65) |
| $T_{max}$ (h; p.o) | 6.75 (50.4) | 8.73 (69.3) | 10.0 (95.2) |
| $AUC_{0-t\,h}$ (ng · h/ml) | 327 (31) | 938 (33.1) | 1328 (25.9) |
| AUC/dosage | 2300 (19) | 5401 (37) | 4710 (15) |
| $AUC_{0-\infty}$ (ng · h/ml) | 570 (36) | 1164 (34) | 1719 (25.4) |
| $t_{1/2}$ (h) | 88.9 (22) | 92.0 (13.3) | 96.7 (15.0) |
| MRT (h) | 142 (20) | 162 (26) | 163 (20.5) |

When the capsule of Compound I dihydrochloride was orally administrated, the average peak time ($T_{max}$) of the plasma concentration was 8 h (4 h-10 h), the plasma concentration at 240 h (i.e. 10 days) after administration was ¹⁄₁₀ of the highest plasma concentration ($C_{max}$); and the highest plasma concentration ($C_{max}$) increased as the administration dose increased. The half-life period ($t_{1/2}$) of Compound I is long (80 h-100 h). The urine excretion amount was less than 1% of the amount of the oral dose.

(2) Pharmacokinetics of Continuous Administration

The qualified subjects took the drug once and performed pharmacokinetic monitor of single administration. After subjecting to at least 7 days of a washout period, pharmacokinetic studies of continuous administration were performed. One treating cycle has continuous administration for 2 weeks and rest for 1 week, and continuous monitor were applied for at least 2 cycles. A total of 21 subjects in 3 dose groups (10 mg, 16 mg and 12 mg, respectively) continuously took the capsules of Compound I dihydrochloride, while performing the monitor of plasma concentration. FIG. 1 (right) shows that the average concentration-time curve of each dose group. Table 2 shows that the pharmacokinetic parameters evaluated based on FIG. 1 (right).

It can be seen from FIG. 1 (right) that when the above daily dosages were used to perform continuous administration for 2 weeks and rest for 1 week, the plasma concentration reached a peak value at 14 days after administration. In the subsequent cycles, the plasma concentration after administration was controlled at 100 ng/ml or lower, the drug accumulation degree was controllable, and benefits were obtained when treating various tumours.

TABLE 2

The pharmacokinetic parameters of Compound I estimated after the continuous administration for 2 weeks and rest for 1 week

| The pharmacokinetic parameters | Average (RSD %) | | |
|---|---|---|---|
| | 10 mg/person (n = 3) | 12 mg/person (n = 15) | 16 mg/person (n = 3) |
| $C_{max}$ (ng/mL) | 64.9 (44.5) | 67.0 (29.0) | 93.1 (29.3) |
| $C_{max}$/dosage | 388 (45) | 361 (32) | 300 (31) |
| $AUC_{0-43天}$ (ng · h/mL) | 1545 (56) | 1500 (27) | 2212 (35) |
| AUC/dosage | 9234 (56) | 8272 (32) | 7109 (36) |

It will be apparent to those skilled in the art that various modifications and variations of the method, the pharmaceutical composition and the medicinal kitmedicinal kit of the present invention can be made without departing from the scope and spirit of the present invention. Therefore, the present invention covers the modifications and variations of this invention provided they come within the scope of the appended claims and their equivalents.

What is claimed is:

1. A method for treating tumors in a patient, the method comprising administering to a patient a daily dose of 5 mg to 20 mg of 1-[[[4-(4-fluoro-2-methyl-1H-indol-5-yl)oxy-6-methoxyquinolin-7-yl]oxy]methyl]cyclopropylamine or a pharmaceutically acceptable salt thereof to the patient via interval administration, wherein the interval administration includes administration periods and rest periods;
   wherein the tumors are liver cancer, breast cancer, kidney cancer, colorectal cancer, non-small cell lung cancer, gastrointestinal stromal tumor, medullary thyroid carcinoma and soft tissue sarcoma.

2. The method according to claim 1, wherein the ratio of the administration periods to the rest periods in days is 2:0.5-5.

3. The method according to claim 2, wherein the interval administration is performed via an administration regimen selected from the group consisting of:
   continuous administration for 14 days and rest for 14 days, followed by continuous administration for 14 days and rest for 14 days;
   continuous administration for 14 days and rest for 7 days, followed by continuous administration for 14 days and rest for 7 days; or
   continuous administration for 5 days and rest for 2 days, followed by continuous administration for 5 days and rest for 2 days.

4. A method for treating tumors, the method comprising an interval administration of 1-[[[4-(4-fluoro-2-methyl-1H-indol-5-yl)oxy-6-methoxyquinolin-7-yl]oxy]methyl]cyclopropylamine or a pharmaceutically acceptable salt thereof to patients;
   wherein the tumors are liver cancer, breast cancer, kidney cancer, colorectal cancer, non-small cell lung cancer, gastrointestinal stromal tumor, medullary thyroid carcinoma and soft tissue sarcoma.

5. The method according to claim 4, wherein the plasma concentration of 1-[[[4-(4-fluoro-2-methyl-1H-indol-5-yl)oxy-6-methoxyquinolin-7-yl]oxy]methyl]cyclopropylamine is 100 ng/ml or lower.

6. The method according to claim 4, wherein the interval administration includes administration periods and rest periods.

7. The method according to claim 6, wherein the ratio of the administration periods to the rest periods in days is 2:0.5-5.

8. The method according to claim 7, wherein the interval administration is performed via an administration regimen selected from the group consisting of:
   continuous administration for 14 days and rest for 14 days, followed by continuous administration for 14 days and rest for 14 days;
   continuous administration for 14 days and rest for 7 days, followed by continuous administration for 14 days and rest for 7 days; or
   continuous administration for 5 days and rest for 2 days, followed by continuous administration for 5 days and rest for 2 days.

9. The method according to claim 4, the daily dosage of 5 mg-20 mg of 1-[[[4-(4-fluoro-2-methyl-1H-indol-5-yl)oxy-6-methoxyquinolin-7-yl]oxy]methyl]cyclopropylamine or a pharmaceutically acceptable salt thereof is administrated.

10. A method for treating tumors, the method comprises an interval administration of a pharmaceutical composition comprising 5 mg-20 mg of 1- [[[4-(4-fluoro-2-methyl-1H-indol-5-yl)oxy-6-methoxyquinolin-7-yl]oxy]methyl]cyclopropylamine or a pharmaceutically acceptable salt thereof to patients;
    wherein the tumors are liver cancer, breast cancer, kidney cancer, colorectal cancer, non-small cell lung cancer, gastrointestinal stromal tumor, medullary thyroid carcinoma and soft tissue sarcoma.

11. The method according to claim 10, wherein the pharmaceutical composition is formulated into a form of single dosage.

12. The method according to claim 10, wherein the pharmaceutical composition is administrated to the patients according to an administration regimen selected from the group consisting of:
    continuous administrating for 2 weeks and resting for 2 weeks;
    continuous administrating for 2 weeks and resting for 1 week; and/or
    continuous administrating for 5 days and resting for 2 days.

13. The method according to claim 10, wherein the pharmaceutical composition is tablets or capsules suitable for oral administration.

14. The method according to claim 10, wherein the pharmaceutical composition is administered once daily according to the regimen of continuously administrating for 2 weeks and resting for 1 week.

15. The method according to claim 10, wherein the method comprises an interval administration of a pharmaceutical composition comprising 5 mg-20 mg of 1-[[[4-(4-fluoro-2-methyl-1H-indol-5-yl)oxy-6-methoxyquinolin-7-yl]oxy]methyl]cyclopropylamine dihydrochloride to patients.

* * * * *